US010776917B2

(12) United States Patent
Allmendinger et al.

(10) Patent No.: US 10,776,917 B2
(45) Date of Patent: Sep. 15, 2020

(54) METHOD AND SYSTEM FOR COMPENSATING FOR MOTION ARTIFACTS BY MEANS OF MACHINE LEARNING

(71) Applicant: Siemens Healthcare GmbH, Erlangen (DE)

(72) Inventors: Thomas Allmendinger, Forchheim (DE); Bernhard Schmidt, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 141 days.

(21) Appl. No.: 16/169,134

(22) Filed: Oct. 24, 2018

(65) Prior Publication Data
US 2019/0130571 A1 May 2, 2019

(30) Foreign Application Priority Data
Oct. 27, 2017 (DE) .................. 10 2017 219 307

(51) Int. Cl.
*G06T 7/00* (2017.01)
*G06T 5/00* (2006.01)
(Continued)

(52) U.S. Cl.
CPC .......... *G06T 7/0014* (2013.01); *A61B 6/5264* (2013.01); *A61B 6/54* (2013.01);
(Continued)

(58) Field of Classification Search
CPC ......... G06T 7/0014; G06T 7/20; G06T 5/003; G06T 11/008; G06T 2207/10016;
(Continued)

(56) References Cited

U.S. PATENT DOCUMENTS 10,631,814 B2 * 4/2020 Ertel .................... A61B 6/5247
2003/0163039 A1 * 8/2003 Pan ........................ A61B 6/541
600/425
(Continued)

FOREIGN PATENT DOCUMENTS

CN          104680491 A      6/2015
CN          106096605 A     11/2016
(Continued)

OTHER PUBLICATIONS

Lecun, Yann et al.; "Gradient-Based Learning Applied to Document Recognition" Proceedings of the IEEE, vol. 86, No. 11, pp. 2278-2324, Nov. 1998; DOI: 10.1109/5.726791; 1998.
(Continued)

*Primary Examiner* — Christopher M Brandt
(74) *Attorney, Agent, or Firm* — Harness, Dickey & Pierce, P.L.C.

(57) ABSTRACT

A method is for training a convolutional neural network of a compensation unit. The method includes: provisioning a machine learning device, the machine learning device being designed for training the convolutional neural network; provisioning a start compensation unit, including an untrained convolutional neural network, on or at the machine learning device; provisioning a training image dataset including a plurality of medical training input images and at least one training output image, wherein a reference object is shown essentially without motion artifacts in the at least one training output image and the reference object concerned is contained in the plurality of medical training input images with different motion artifacts; and training the convolutional neural network of the compensation unit in accordance with a principle of machine learning, using the training image dataset. A compensation unit, a machine
(Continued)

learning device, a control device for controlling a medical imaging system are also disclosed.

22 Claims, 6 Drawing Sheets

(51) Int. Cl.
- A61B 6/00 (2006.01)
- G06T 7/20 (2017.01)
- G06N 3/08 (2006.01)
- G06T 11/00 (2006.01)
- A61B 6/03 (2006.01)

(52) U.S. Cl.
CPC ............... G06N 3/08 (2013.01); G06T 5/003 (2013.01); G06T 7/20 (2013.01); G06T 11/008 (2013.01); A61B 6/032 (2013.01); G06T 2207/10016 (2013.01); G06T 2207/10072 (2013.01); G06T 2207/10116 (2013.01); G06T 2207/20081 (2013.01); G06T 2207/20084 (2013.01); G06T 2207/20201 (2013.01); G06T 2207/30048 (2013.01)

(58) Field of Classification Search
CPC . G06T 2207/20201; G06T 2207/30048; G06T 2207/20084; G06T 2207/20081; G06T 2207/10116; G06T 2207/10072; A61B 6/5264; A61B 6/54; A61B 6/032; G06N 3/08; G06N 3/0454

See application file for complete search history.

(56) References Cited

U.S. PATENT DOCUMENTS

| | | | | |
|---|---|---|---|---|
| 2006/0193430 | A1* | 8/2006 | Kuhn | A61B 6/032 378/9 |
| 2009/0015695 | A1* | 1/2009 | Dunki-Jacobs | G06T 5/003 348/241 |
| 2012/0230556 | A1* | 9/2012 | Wollenweber | G06T 11/008 382/128 |
| 2013/0100314 | A1* | 4/2013 | Li | H04N 5/2355 348/229.1 |
| 2014/0376789 | A1* | 12/2014 | Xu | G06T 7/0016 382/128 |
| 2015/0116525 | A1* | 4/2015 | Peng | H04N 5/23254 348/218.1 |
| 2015/0154741 | A1* | 6/2015 | Chen | G06T 5/001 348/77 |
| 2015/0265220 | A1* | 9/2015 | Ernst | G06T 7/292 600/411 |
| 2016/0095565 | A1 | 4/2016 | Fenchel | |
| 2016/0345926 | A1* | 12/2016 | Dutta | A61B 6/032 |
| 2017/0074959 | A1* | 3/2017 | Li | G01R 33/56509 |
| 2017/0196522 | A1* | 7/2017 | Gupta | A61B 6/4429 |
| 2017/0323433 | A1* | 11/2017 | Ukil | G06T 7/254 |
| 2018/0100907 | A1 | 4/2018 | Soza et al. | |
| 2018/0192098 | A1* | 7/2018 | Pekkucuksen | G06T 5/50 |
| 2018/0374245 | A1* | 12/2018 | Xu | G06T 11/008 |
| 2019/0108441 | A1* | 4/2019 | Thibault | G06T 11/008 |
| 2019/0328341 | A1* | 10/2019 | Katsevich | A61B 6/486 |
| 2020/0129263 | A1* | 4/2020 | Izadyyazdanabadi | A61B 90/361 |

FOREIGN PATENT DOCUMENTS

| | | |
|---|---|---|
| DE | 102014219915 B3 | 11/2015 |
| DE | 102016219887 A1 | 4/2018 |

OTHER PUBLICATIONS

Fischer, Philipp et al. "FlowNet: Learning Optical Flow with Convolutional Networks" arXiv:1504.06852; IEEE International Conference on Computer Vision (ICCV), 2015; https://arxiv.org/abs/1504.06852v2; DOI: 10.1109/ICCV.2015.316; Electronic ISSN: 2380-7504.

German Office Action for DE 102017219307.7 dated Aug. 14, 2018.
German Office Action and English translation there of dated Aug. 14, 2018.
German Decision to Grant and English translation thereof dated Mar. 28, 2019.
Chinese Office Action dated Sep. 30, 2019.

* cited by examiner

METHOD AND SYSTEM FOR COMPENSATING FOR MOTION ARTIFACTS BY MEANS OF MACHINE LEARNING

PRIORITY STATEMENT

The present application hereby claims priority under 35 U.S.C. § 119 to German patent application number DE 102017219307.7 filed Oct. 27, 2017, the entire contents of which are hereby incorporated herein by reference.

FIELD

Embodiments of the invention generally relate to a method for creating a compensation unit for automatically compensating for motion artifacts in a recorded medical image or to a compensation unit as well as a machine learning device for this purpose. Furthermore embodiments of the invention generally relate to an identification method for automatic recognition of and if necessary also for compensation for motion artifacts in a recorded medical image while using such a compensation unit, a control device for controlling a medical imaging system as well as a corresponding medical imaging system. A recorded image within the framework of embodiments of the invention can be a digital image, meaning that it comprises image data or consists of image data.

BACKGROUND

In imaging methods in medicine, for creating each pixel of a recorded image, the method mostly relies on evaluating a measured value that has been recorded in a specific time interval. Thus for example Computed Tomography ("CT") detects the local x-ray attenuation of the body structure of the patient integrated over the recording time. In this case the recording time mostly lies in the order of magnitude of 1 second.

Because of the integration of the measurement signals over the recording time, the motion of objects, which as rule represent organs of a human or animal patient, is a serious problem in medical imaging. As a rule, in medical images that record an image of an object moving during the recording there are always motion artifacts in the area of the recorded object. For example during a recording of the heart with a CT or other recording method, its motion leads to difficulties in the imaging resolution of structures, e.g. of the coronary arteries located on this heart.

This problem can be countered with a simple shortening of the recording time, but as a rule this has a disadvantageous effect on the signal-to-noise ratio or, with an increase in the intensity related to this, on the radiation load (with a CT or corresponding recording method) or the load caused by a variable magnetic field (e.g. for recordings made by a Magnetic Resonance Tomograph MRT).

As well as technical solutions such as e.g. faster rotation times and dual-source CT technology for optimizing the time resolution, a plurality of software-based solutions have been developed in recent years.

Within the very broad field of motion-compensated reconstruction of recordings of the heart, a frequent common factor is the explicit determination of 4D vector fields, which describe the spatial and temporal course of the heart motion, in order to then employ these subsequently within the framework of a motion-compensating reconstruction. Differences between the known methods primarily lie in whether 4D fields are to be determined directly from multiphase reconstructions or whether these are implicitly included in the reconstruction as free parameters within the framework of a minimization method with the aid of a suitable target metric, e.g. with methods such as SnapShot Freeze, Motion Artifact Metric method (MAM) or Motion Compensation based on Partial Angle Reconstructions (PAMoCo).

A common element in these methods is that a heavy local restriction of the correction for limiting the degrees of freedom is needed, wherein frequently the regions of the coronary arteries that have been obtained by way of segmentation from a standard reconstruction are selected. As an alternative thereto there are also approaches that model the motion of the complete heart muscle.

SUMMARY

The inventors have discovered that a disadvantage of the prior art is that the steps carried out as a rule, of standard reconstruction, segmentation (e.g. of the coronary artery tree) and the local restriction of the reconstruction itself are negatively affected as a rule by motion artifacts.

At least one embodiment of the present invention provides an alternate, more convenient, method for compensating for motion artifacts and a corresponding compensation unit as well as a control device for automatic control of a medical imaging facility, with which at least one of the disadvantages described above can be avoided or at least reduced and motion artifacts can be recognized in an automated and safe way. At least one embodiment of the present invention further provides a compensation unit and corresponding processing devices.

Embodiments of the present invention are directed to a method, a compensation unit, a machine learning device, an identification method, a control device and also a medical imaging system.

Embodiments of a solution to the problem illustrated above are very complex and it is not possible to effectively compensate for motion artifacts in a simple way. Also an embodiment of an inventive compensation unit cannot be produced in a simple way. Therefore embodiments of the invention comprises not only the compensation unit or a method for compensating for motion artifacts with this compensation unit, but also the production of this compensation unit and of the processing device relating thereto. Also, at the same time, the compensation offers the opportunity of recognizing motion artifacts and if necessary also of eliminating them or of controlling a medical imaging device accordingly. This too is part of at least one embodiment of the invention.

At least one embodiment is directed to method for training convolutional neural network of a compensation unit, the method comprising:

provisioning a machine learning device, the machine learning device being designed for training the convolutional neural network;

provisioning a start compensation unit, including an untrained convolutional neural network, on or at the machine learning device;

provisioning a training image dataset including a plurality of medical training input images and at least one training output image, wherein a reference object is shown essentially without motion artifacts in the at least one training output image and the reference object concerned is contained in the plurality of medical training input images with different motion artifacts; and training the convolutional neural network of the compensation unit in accordance with a principle of machine learning, using the training image dataset.

At least one embodiment is directed to a compensation unit for at least one of automatic identification of motion artifacts and compensation for motion artifacts in a recorded medical image, comprising:

a convolutional neural network, trained by at least:
provisioning a machine learning device, the machine learning device being designed for training the convolutional neural network;
provisioning a start compensation unit, including an untrained convolutional neural network, on or at the machine learning device;
provisioning a training image dataset including a plurality of medical training input images and at least one training output image, wherein a reference object is shown essentially without motion artifacts in the at least one training output image and the reference object concerned is contained in the plurality of medical training input images with different motion artifacts; and
training the convolutional neural network of the compensation unit in accordance with a principle of machine learning, using the training image dataset.

At least one embodiment is directed to a machine learning device, comprising:

a processor; and
a data memory, storing instructions which, when executed, configured the processor to at least:
enter a training image dataset provided to the processor into a convolutional neural network;
operate the convolutional neural network; and
train a start compensation unit with an untrained convolutional neural network according to a method for training convolutional neural network of a compensation unit, the method comprising:
provisioning a machine learning device, the machine learning device being designed for training the convolutional neural network;
provisioning a start compensation unit, including an untrained convolutional neural network, on or at the machine learning device;
provisioning a training image dataset including a plurality of medical training input images and at least one training output image, wherein a reference object is shown essentially without motion artifacts in the at least one training output image and the reference object concerned is contained in the plurality of medical training input images with different motion artifacts; and
training the convolutional neural network of the compensation unit in accordance with a principle of machine learning, using the training image dataset.

At least one embodiment is directed to an identification method for automatic recognition of motion artifacts in a recorded medical image, comprising:

provisioning a compensation unit with a neural network with a convolutional neural network trained by the method of at least one embodiment;
provisioning at least one recorded medical image;
recognizing motion artifacts in the at least one recorded medical image via the compensation unit, by processing the at least one recorded medical image with the convolutional neural network; and
creating result data with at least one of identification and reduction of the motion artifacts recognized.

At least one embodiment is directed to a control device for controlling a medical imaging system, comprising:

at least one processor to designed to carry out the identification method of at least one embodiment of the present application.

At least one embodiment is directed to a medical imaging system, comprising:

the control device of at least one embodiment of the present application.

At least one embodiment is directed to a non-transitory computer program product storing a computer program, directly loadable into a memory device of a processing system or of a control device of a medical imaging system, the computer program including program sections for carrying out the method of at least one embodiment of the present application when the computer program is executed in the processing system or the control device.

At least one embodiment is directed to a non-transitory computer-readable medium, storing program sections readable in and executable by a processing unit, to carry out the method of at least one embodiment of the present application when the program sections are executed by the processing unit.

BRIEF DESCRIPTION OF THE DRAWINGS

The invention will be explained once again in greater detail below with reference to the enclosed figures on the basis of example embodiments. In these explanations the same components in the various figures are provided with identical reference numbers. The figures are as a rule not true-to-scale. In the figures.

Figure 1:
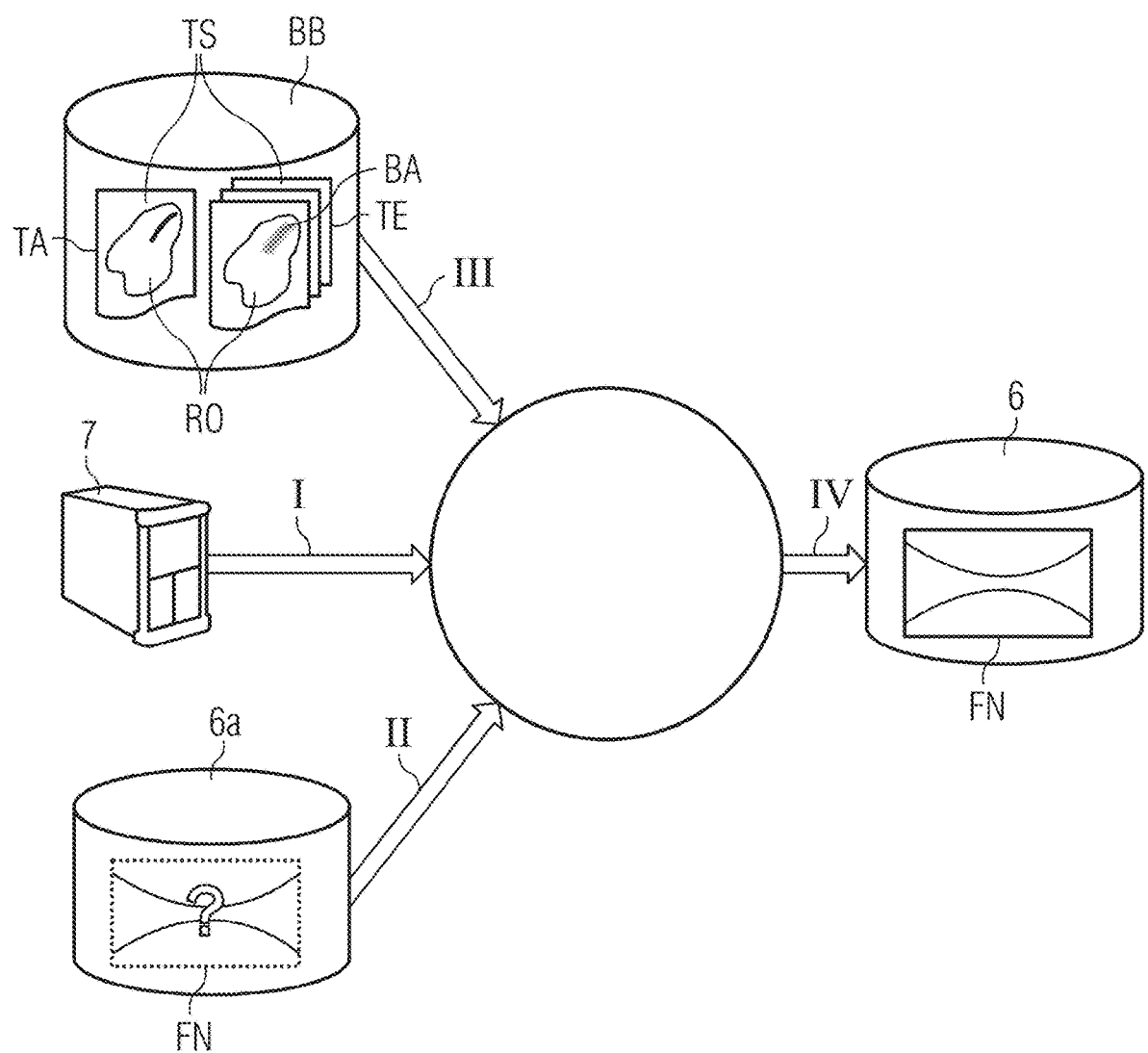
FIG. 1 shows a schematic diagram of a first example embodiment of the inventive method for production of an inventive compensation unit.

It is assumed in the explanations given below that the medical imaging facility or the imaging facility involved is a computed tomography system. Basically however the method is also able to be employed on other imaging systems.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment of the inventive method serves to create a compensation unit for automatic identification and/or compensation for motion artifacts in a recorded medical image. This recorded image can be recorded via a medical imaging system and is e.g. an image recorded by a Computed Tomograph (CT) or a Magnetic Resonance Tomograph (MRT). For example the recorded image of a heart, which by its beating causes image artifacts on the recordings, can be a suitable recorded image for at least one embodiment of the invention. Both reconstructed recordings and also raw datasets can be used for the recorded images, for example spectral CT raw datasets or CT images reconstructed therefrom.

The method, of at least one embodiment, for training the compensation unit comprises:
Provision of a machine learning device;
Provision of a start compensation unit;
Provision of a training image dataset; and
Training of the convolutional neural network.
Provision of a Machine Learning Device Such a machine learning device will be described in greater detail further in the embodiments below. The machine learning device is designed for training a convolutional neural network.

A Convolutional Neural Network (CNN) is basically known to the person skilled in the art. Since a detailed presentation of the architecture of such networks would go beyond the framework of this description, the reader is referred to the two standard scientific publications "FlowNet: Learning Optical Flow with Convolutional Networks" (Philipp Fischer et al.; e.g. to be found at: https://arxiv.org/abs/1504.06852v2) and "Gradient-Based Learning Applied to Document Recognition" (Yann LeCun et al.; Proceedings of the IEEE, 86(11):2278-2324, November 1998), the entire convents of which are each hereby incorporated herein by reference. Such convolutional neural networks initially carry out a series of convolutional and so-called pooling steps, before the data obtained thereby is deconvoluted again and so-called unpooling steps are carried out. The convolution and deconvolution is carried out with matrixes, which are also referred to as "kernels". Between the convolution and the deconvolution there can be an almost one-dimensional range of numbers, which is often referred to as a fully connected layer.

Provision of a Start Compensation Unit.

The start compensation unit is the later compensation unit, which however has not yet been trained or has not yet been optimally trained. It is provided on or at the machine learning device and is embodied to be trained via machine learning (by the processing device). The start compensation unit comprises an untrained convolutional neural network.

Provision of a Training Image Dataset.

This training image dataset can be provided by way of an image data library, which can also be referred to as a training library. The training image dataset comprises a plurality of medical training input images and at least one training output image, which can be real images of a medical imaging system or also artificially generated images.

A reference object essentially without motion artifacts is contained here in the training output images. The reference object concerned is contained in the training input images with various motion artifacts. Since training output images represent a desired, possibly idealized, target image, they can also be referred to as desired images, (required) target images or ideal images.

The training image dataset comprises images, i.e. image data, wherein the training output images can also contain classification objects. The latter are data able to be understood by a computer about the type of structures, e.g. structures are designated as "heart", "coronary arteries" or even as "motion artifact" processable for the computer (e.g. in the form of an ontology). The image data library can be a database with a set of training recordings for example, which has a link for data processing to the machine learning device. A suitable medical imaging system for recording training input images can be a Computed Tomograph (CT) for example.

For example simulations with motion artifacts (training input images) and without motion artifacts (training output images) of the same object are created and the network is thus trained.

Another example is the use of true images of the patient. In this case images from "bad" phases with marked motion artifacts can be used as training input images and "good" images, essentially without or with very small motion artifacts, can be used as training output images. For example images with individual motion phases can also be overlaid on one another, in order to create motion artifacts, and the individual images can serve as training output images (or control images).

By contrast with the later identification method, which essentially only needs one recorded image as input, both the input and also the output must be specified to the convolutional neural network during training.

Training of the Convolutional Neural Network.

The convolutional neural network of the compensation unit is trained here in accordance with the principle of machine learning using the training image dataset.

The formulation of a "recorded image (of a medical imaging system)" used previously and hereafter in this document is to be understood as a recorded image of an object, for example of an organ, a part of the body and/or region of a patient, (also referred to as a "motif"), which has been created by way of a medical imaging system. This can involve two-dimensional images or image data, volume image data or also an image dataset consisting of a plurality of image data, e.g. a stack of two-dimensional image data.

An inventive compensation unit of at least one embodiment is suitable for or designed for automatically identifying and/or compensating for motion artifacts in a recorded medical image. It comprises a convolutional neural network, which has been produced or trained with at least one embodiment of the inventive method. At least one embodiment of the inventive compensation unit has thus been created in accordance with the principle of machine learning from a start compensation unit, wherein the training was carried out on the basis of the recognition of motion artifacts in a training image dataset provided.

At least one embodiment of the compensation unit could also be referred to as an "identification unit" (see below "identification method"), in order to particularly highlight the capability for identification of motion artifacts, which is fundamentally needed to compensate for them. Since however in practice the unit is likely to be used for automatically compensating for motion artifacts, it will continue to be referred to hereafter as a "compensation unit", without however excluding the possibility of a pure identification therewith.

An inventive machine learning device of at least one embodiment comprises a processor and a data memory with instructions, which, when executed, make it possible for the processor to enter a training image dataset, provided to the processing device, into a convolutional neural network, to operate a convolutional neural network, and to train a start compensation unit with an untrained convolutional neural network according to at least one embodiment of the inventive method. This means that the machine learning device is designed for example to carry out convolution operations or their inverse functions in accordance with the principle of training convolutional neural networks. In particular the machine learning device is designed for operation and for programming of FPGAs.

At least one embodiment of an inventive identification method is suitable for or is designed for automatic recognition and if necessary also for automatically compensating for motion artifacts in a recorded medical image. The recorded image originates in such cases as a rule from a medical imaging system and is e.g. a CT recording or comprises projection data. The identification method can, in particular when it serves primarily to compensate for motion artifacts, also be referred to as a "compensation method" (cf. the discussion above about the designation "compensation unit"). The identification method comprises:

Provision of a compensation unit;
Provision of a recorded image;
Recognition of motion artifacts; and
Creation of result data.
Provision of a Compensation Unit.

At least one embodiment of the inventive compensation unit comprises a trained convolutional neural network. The production of such a trained compensation unit has been described in at least one embodiment within the framework of at least one embodiment of the inventive method for training the compensation unit.

Provision of a Recorded Image.

At least one recorded medical image is provided, which has been recorded in particular by a medical imaging system.

Recognition of Motion Artifacts.

Image artifacts are now identified (recognized) in the recorded medical image via the compensation unit within the framework of a processing of the recorded image by the convolutional neural network.

Creation of Result Data.

In the result data the recognized motion artifacts are identified or automatically reduced or compensated for. The result data in this case preferably comprises result images and/or classification objects (see description of the result data further below).

The identified motion artifacts can e.g. be simply designated with markers. But also motion artifact objects can be inserted at the positions concerned and thus elements that the computer can understand can be added to the resulting image. The identification can be done directly in the recorded image or in an additional representation, e.g. an additional image layer.

A processing of the recorded image can be carried out as an alternative or in addition thereto, wherein an elimination or reduction (both terms are covered by the designation "compensation") of motion artifacts is undertaken. For example an automatic removal of motion artifacts could be carried out in the imaging of coronary arteries on the beating heart.

In this way for example sources of errors caused by motion artifacts could be reduced by training the compensation unit with a large quantity of suitable datasets, and in this way the quality of the recorded images improved beyond the conventional level.

At least one embodiment of an inventive control device for controlling a medical imaging system is designed for carrying out at least one embodiment of an inventive identification method or is equipped with at least one embodiment of an inventive compensation unit.

At least one embodiment an inventive medical imaging system comprises at least one embodiment of an inventive control device.

A large part of the aforementioned components of embodiments of the machine learning device, of the compensation unit and/or of the control device, can be realized entirely or in part in the form of software modules in a processor of a corresponding control device or of a processing device. A largely software-based realization has the advantage that even control devices or processing devices already used previously can be upgraded by a software update, in order to operate in the inventive way.

To this extent, at least one embodiment is also achieved by a corresponding computer program product with a computer program, which is able to be loaded directly into a memory device of a processing device or of a control device, e.g. of a Computed Tomography system, with program sections for carrying out all steps of the inventive method when the program is executed in the control device or processing device. Such a computer program product, along with the computer program, can if necessary comprise additional elements, such as e.g. documentation and/or additional components, including hardware components, such as e.g. hardware keys (dongles etc.) for use of the software.

For transport to the control device or the processing device and/or for storage at or in the processing or control device, a computer-readable medium, for example a memory stick, a hard disk or another transportable or permanently-installed data medium, on which program sections of the computer program able to be read in and executed by the processing or control device are stored, can be used. The processing unit can e.g. have one or more microprocessors or the like interacting with one another for this purpose.

Therefore a compensation unit in the form of a computer program product with a computer program is also preferred, which is able to be loaded directly into a memory device of a processing system or a control device of a medical imaging system, with program sections for carrying out all steps of the inventive compensation method when the computer program is executed in the processing system or the control device.

Also preferred is a compensation unit in the form of a computer-readable medium, on which program sections able to be read in or carried out by a processing unit are stored, for carrying out all steps of at least one embodiment of an inventive identification method when the program sections are executed by the processing unit. The compensation unit can also be present in the form of this computer-readable medium as hardware, e.g. as a programmed EPROM or as an FPGA (Field Programmable Gate Array).

Further, especially advantageous embodiments and developments of the invention emerge from the claims as well as from the description given below, wherein the claims of one claim category can also be developed analogously to the claims and parts of the description for another claim category and in particular also individual features of different example embodiments or variants can be combined to form new example embodiments or variants.

In an example embodiment, a method the training image dataset comprises a number of training output images, in which the reference object is shown in each case in different phases of its motion. This has the advantage that a complete motion profile can be created and motion artifacts over the entire motion period can be recognized and compensated for.

For example a plurality of CT images can be used as training output images, which show an organ in its different stages of motion. The number of the training output images preferably amounts to a value that corresponds to the time of the motion period divided by the average recording time. For this form of embodiment it is especially advantageous if a plurality of training input images is present for each section of the motion phases of the object, i.e. for each training output image.

If real recordings are used for training it is preferred that the same object (organ) is reconstructed at a number of different points in time and in this way a temporal sequence of images is created. Even if only one object has been referred to above, it is especially preferred to train the convolutional network on a number of different objects or to divide the main object (e.g. "heart") into a number of part objects, (e.g. left coronary, right coronaries, aorta valve, . . . ). For example a number of images of the aorta valve with motion artifacts (training input images) distributed over a period of time of e.g. 1 second, together with an image without motions (training output image), can form one training set. A corresponding procedure could then be undertaken with the left coronary and other objects.

Preferably the reference object is annotated in the training output image. As an alternative or in addition, the training output image comprises information about at least one classification object of the reference object.

The training can be carried out according to the "pixel-by-pixel" principle, i.e. a classification object is assigned for each pixel of the training input image on the training output image, e.g. "background", "vessel", "motion artifact" but also "unknown" or "not recognized".

Preferably the training image dataset is designed so that the training input images comprise part images of an overall image and in combination produce the overall image. The training output image preferably contains the object shown on the overall image, which is not initially absolutely necessary however, since this is also able to be reconstructed during the learning process. This is especially advantageous for the use of real recordings for training, since the recording time for the individual images reduces.

Preferably the training image dataset comprises computed tomography or x-ray images, in particular of a dual-source CT or multi-source CT. With these devices recordings of CT images are normally carried out with a number of different x-ray energies. They can also be used however to create two or more recordings from different angles at the same time with the same x-ray energies.

While normal CTs have a time resolution of for example 130 ms for a 180° reconstruction, dual-source devices can make this reconstruction possible within 66 ms, in that they simultaneously create two recordings offset by 90° with a reconstruction angle of 90° in each case, which are combined in a subsequent step. The compensation unit could also be trained with clinical data of a dual-source device, while it would be used in the application for single-source device with only one detector. A inverse usage could likewise offer advantages however, depending on application case.

Within this context is also preferred that individual training input images (or also a large part or all) have a reconstruction angle of <180°, wherein the sum of a number of training input images again produces a reconstruction angle of 180° however, i.e. a complete image.

This produces an improved time resolution, since the time interval for a recording is shortened.

For example in the case of a single-source system, an image of the heart with overall 180° of parallel equivalent data could be combined from 6 images at 30° each. In the case of a dual-source system only around 90° per system will be needed, so that here 6 images at 15° could be created. The sum of all 12 part images would produce a complete CT image.

The result data could comprise a result image and/or at least a classification object.

A result image refers to an image which corresponds to the recorded image provided or (e.g. in the case of a number of part images that produce an overall image) to a sum of a number recorded images provided, i.e. a graphical reproduction of the recorded motif. However motion artifacts are identified in the result image with the aid of the inventive identification method, e.g. by markers or by showing the motion artifact in a separate image layer, and/or compensated for, i.e. have been removed. Especially preferred is a combination of marking and compensation, in which a motion artifact has been removed in an image layer, but continues to be present in a separate image layer and can be shown and hidden as required.

A classification object refers to information that represents a marking for the type of a specific object that can be understood by a computer (see also above for description of the training output image). It can be present as a marker but also as image information or as an abstract object such as e.g. as a term in an ontology. It is especially preferred that the image information is encoded in accordance with the classification object. Basically the classification objects can have all possible forms, provided these can be "understood" or processed by the computer.

For example, in the recording of a heart, the heart can be recognized as a "heart" object, the coronary arteries as a "coronary vessel" object and motion artifacts as a "motion artifact" object. In a possible representation the heart can then bear the label "heart" in a result image, the coronary arteries the label "coronary vessel" and motion artifacts the label "motion artifact", which would represent a combination of result image and classification object. However an image can also be created in which the image elements that are assigned to the heart are identified by a color, those image elements that represent coronary arteries by a second color and motion artifacts by a third color. The color coding would represent a marking here.

It is especially preferred in this context for a result image to be created in which classification objects are present, if necessary in a specific image plane.

Preferably a number of recorded medical images, which are designed so that individual recorded images comprise parts of an overall image and in combination produce the overall image, are provided to at least one embodiment of the identification method.

The overall image in this case can be expressed as a spatial overall image or a temporal overall image. Basically, although there is a time sequence with a number of recordings since these were recorded at different times, the individual recordings of a periodically moving object can however also constantly reproduce the same motion phase, which would be irrelevant in relation to a timing sequence and could be interpreted as simultaneous recordings.

Concerning the expression as a temporal overall image, it is preferred for the part recordings to represent the object in different, especially consecutive, motion phases.

Concerning the expression as a spatial overall image, it is preferred for the part recordings to be parts of a two-dimensional overall image ("slice image") or individual slice images of a three-dimensional overall image.

In the preferred case that the recorded images are computed tomography or x-ray recordings, in particular recordings of a dual-source CT or multi-source CT, it is preferred because of the shorter recording time that individual recorded images have a reconstruction angle of <180°. This reconstruction angle in this case relates to the reconstruction of a slice image, which as a rule amounts to 180° for a complete slice image.

The recorded images of this preferred form of embodiment thus represent part recordings for a two-dimensional overall image. So that the overall image is complete, the sum of a number of the recorded images must however produce an (overall) reconstruction angle of 180°.

For example the recorded images (part recordings) can comprise a reconstruction angle of 30°, wherein overall 6 recorded images (part images) are recorded from different ranges of angles. These 6 recorded images (part images) are then used as input for the inventive identification method, which creates from these images an overall image with a reconstruction angle of 180°. When a dual-source CT is used 6 part images with a reconstruction angle 15° (instead of 30°, i.e. in a shorter recording time) could also be recorded with the two recording units in each case.

Also disclosed in at least one example embodiment is an identification method, which can be used for controlling a medical imaging system. This method comprises the steps:

Provision of a Control Data Library.

Control datasets for the medical imaging system concerned are stored in this control data library.

Selection of a Control Dataset.

The selection of the control datasets is based on a motion artifact recognized in a recorded image and/or on a choice of an object to be recorded. Thus, on identification of a recognized motion artifact, a control dataset is selected that is designed to suppress this motion artifact on recorded images. As an alternative or in addition, a control dataset can also be selected as a function of the object to be recorded. Whether the heart or the liver is to be recorded for example. This control dataset can contain control commands or reconstruction commands, which have been specifically adapted to the motion of the selected object.

Use of the Selected Control Dataset for Creating a Recorded Image or a New Recorded Image of the Motif in Which a Motion Artifact has been Identified.

Please note that the choice of object initially has nothing to do with the motion artifacts. However, because a compensation unit trained on an organ (object) or a number of organs (objects) knows the movement of these organs, a specific recording control can be selected for an organ however, which is optimal for a later identification or compensation for motion artifacts. This has the advantage that, on recognition of a motion artifact or for the choice of an object to be recorded, an optimized control can be applied immediately. For example, through a recognition of the phase of the heart cycle an optimized series of recordings of the heart can be created. It is also possible to select the optimum recording point for part recordings. Moreover it is thus possible, during a movement of an object out of an image plane, because of the identified motion artifact, to deduce the type and direction of the motion and thereby to achieve an automatic adjustment.

An advantage of at least one embodiment of the invention is primarily that it is easy to use. The steps previously frequently carried out first of all, such as e.g. standard reconstruction, segmentation of the coronary artery tree or the local restriction of the reconstruction can be omitted by using at least one embodiment of the invention. A source of errors is thus greatly suppressed, since these steps themselves can be negatively affected by motion artifacts.

Moreover at least one embodiment of the inventive method, through its application at a more global level, enables motion compensation in the image for regions of the anatomy that is not possible today, e.g. a compensation for motion of the heart valves.

Furthermore at least one embodiment of the inventive compensation unit can be present as hardware, e.g. as an FPGA. Such Field Programmable Gate Arrays are freely obtainable and represent an advantageous basis for realization of an inventive compensation unit. The selected FPGA must be trained in this case with at least one embodiment of an inventive method. The trained FPGA can then be used for identification or compensation for motion artifacts.

FIG. 1 shows a schematic diagram of a simple form of an embodiment of the inventive method for production of an inventive compensation unit.

Figure 3:
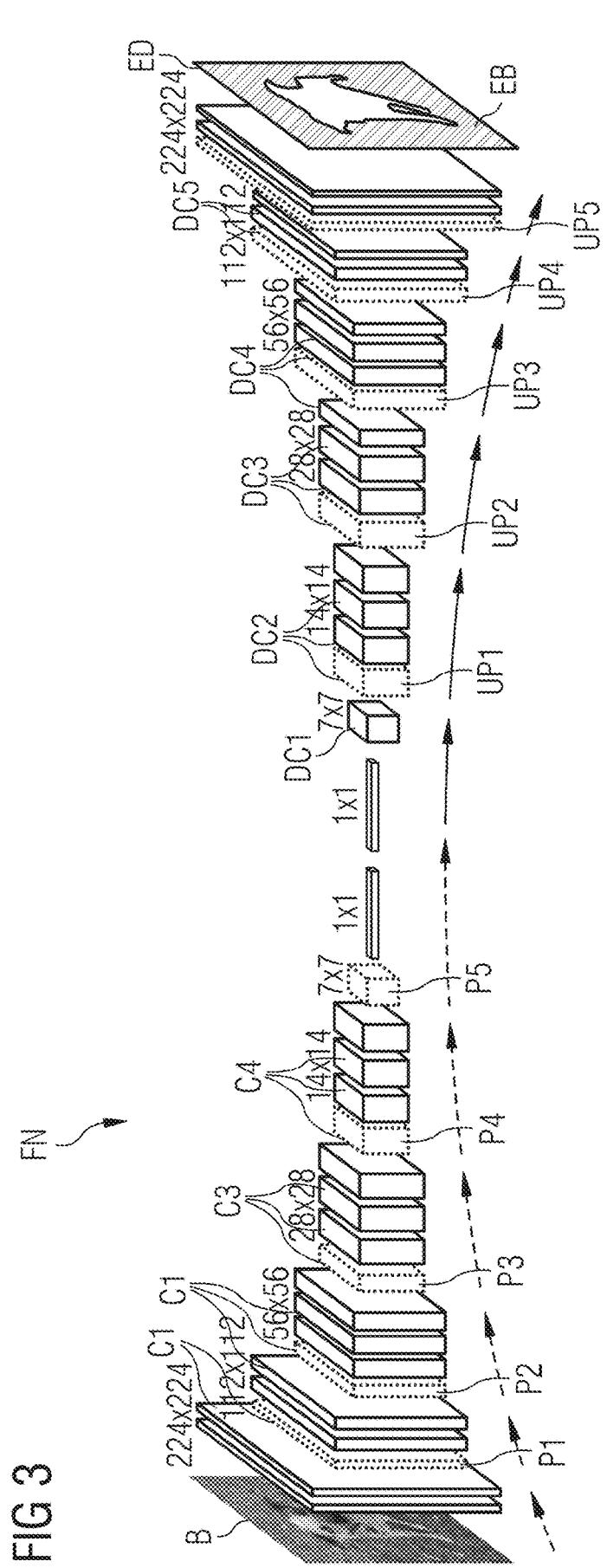
FIG. 3 shows a schematic diagram of a convolutional neuronal network.

In step I a machine learning device 7 is provided, wherein the machine learning device 7 is embodied by way of an algorithm to recognize graphical elements in recorded images or in image data (see also FIG. 4 in this context) and to train a convolutional neural network FN (see also FIG. 3 in this context).

In step II a start compensation unit 6a is provided, which is embodied to be trained via machine learning, and basically represents the untrained compensation unit 6, which is to be represented by a question mark. This start compensation unit 6a is provided in this case on or at the machine learning device 7, i.e. as a data structure connected to this machine learning device 7 for exchange of data, as depicted here, or as a data structure directly in this machine learning device 7.

In step III an image data library BB is provided, comprising a training image dataset TS consisting of training input images TE and at least one training output image TA. These can be recordings of a medical imaging system 1 but can also be artificially created representations. Contained in the training input images TE in such cases are motion artifacts BA, the training output images TA by contrast essentially do not contain any motion artifacts BA or motion artifacts BA are strongly suppressed therein.

The circle in which the three arrows labeled I, II and III converge is the initial state here, for which the three preceding components have been provided. The start compensation unit 6a must now be trained for production of the compensation unit 6.

In step VI this training of the compensation unit 6 takes place in accordance with the principle of machine learning based on the recognition of motion artifacts contained in the training input images TE. The trained compensation unit 6 then comprises the trained convolutional neural network FN.

Figure 2:
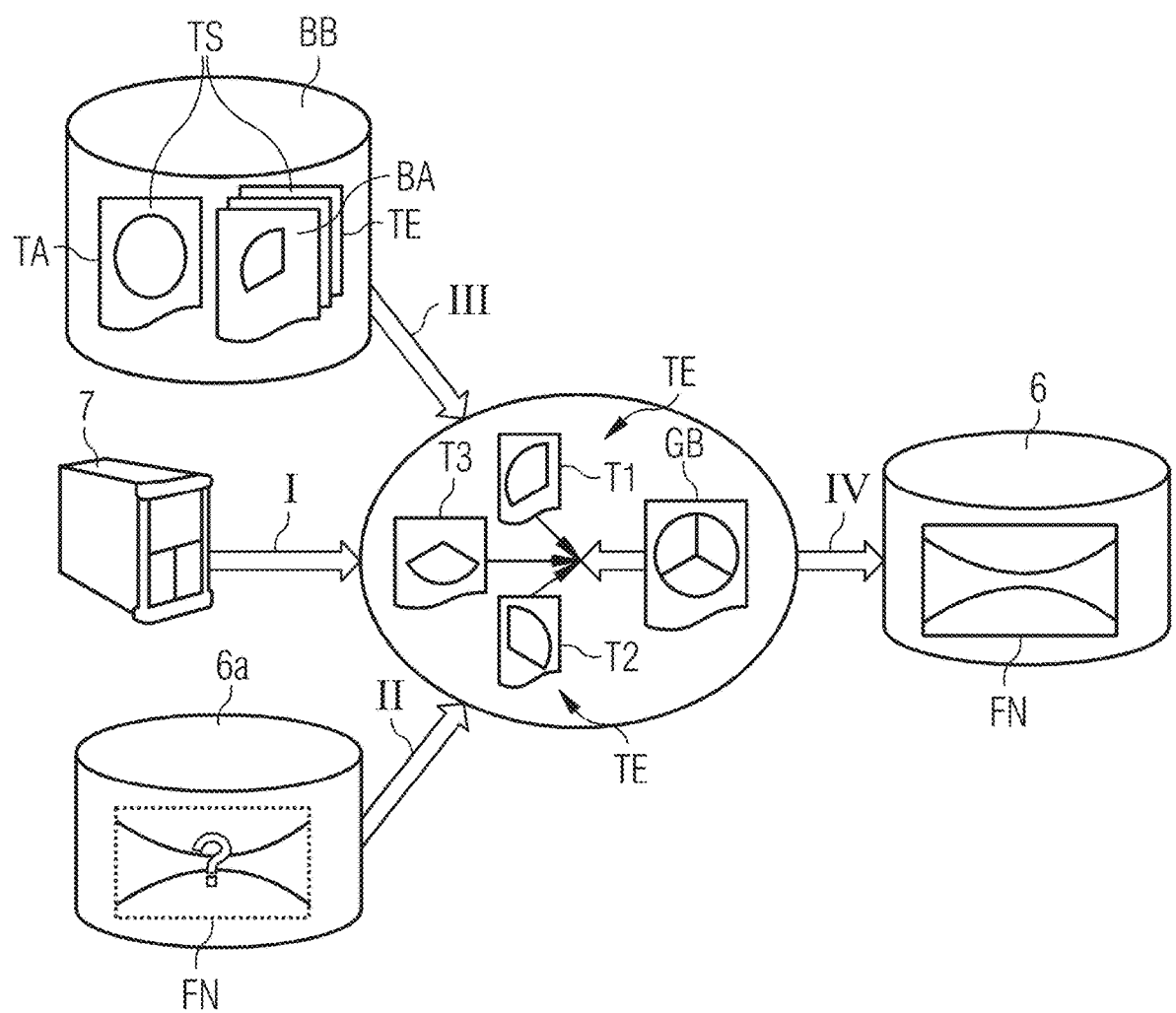
FIG. 2 shows a schematic diagram of a second example embodiment of the inventive method for production of an inventive compensation unit with a training based on part images.

FIG. 2 shows a schematic diagram of an example embodiment of an inventive method for production of an inventive compensation unit 6 with a training based on the part images T1, T2, T3. This can offer advantages if the method is to work later during the identification with recorded images B that have been recorded with a reduced recording time for reduction of motion artifacts BA and therefore merely represent part images of an object O.

This figure basically corresponds to FIG. 1. Here too the steps I, II and III are carried out, wherein in step III however a complete training output image TA is provided, which is represented here by a circle. The training output image TA could in this case represent the object O in the training output image TA of FIG. 1 for example. By contrast with FIG. 1 however the training input images TE do not represent complete objects, which is indicated here by circle segments. In image terms it could be imagined that each circle segment corresponds to a part of the representation of the training input images TE from FIG. 1.

In the central circle of FIG. 2 it is shown how, as part of the training in each case, three training input images TE are combined as part images T1, T2, T3 into an overall image GB. If this form of embodiment is again compared to that from FIG. 1, the reference object RO shown there in the training input image TE could have been cut up in FIG. 2 into three part images T1, T2, T3.

The training of the compensation unit 6 in step IV is based in this case on the comparison of the training output image TA with the constructed overall image GB. Generally it would be possible as an alternative to dispense with the formation of the overall image GB and to enter the part images T1, T2, T3 directly as different layers into the convolutional neural network FN.

FIG. 3 shows a schematic diagram of a convolutional neural network FN. A recorded image B, which is entered into the convolutional neural network FN, is divided as a rule into different layers. With colored images this could be a subdivision into red, green and blue channels for example. However a number of recorded images B (these also include training input images TE) can be entered at the same time into the convolutional network FN, as has already been indicated in the preceding example. For example a number of part images T1, T2, T3 can be entered and form the different layers, which in their totality would represent a complete recorded image BA.

Now a number of pooling steps P1, P2, P3, P4, P5 takes place, which reduces the image information, and convolution steps C1, C2, C3, C4, C5, which create a series of data fields, in which a convolution mask (also referred to as a "kernel"), is guided over the previously created data fields or layers of the recorded image and these are subjected to a convolution operation with the convolution matrix. This process is repeated with a number of different kernels on the individual convolution layers (see method of operation of convolutional networks). The thin blocks after the last pooling step P5 represent the "fully connected layer", which is not absolutely necessary for carrying out the invention however.

Thereafter the deconvolution DC1, DC2, DC3, DC4, DC5 is undertaken and the so-called "unpooling" UP1, UP2, UP3, UP4, UP5. In this case an inversion of the preceding convolution and of the pooling is basically carried out, without however absolutely having to use the actual inversion functions. This can likewise be done with matrixes, which in this case thus also do not absolutely have to be inversion functions of the matrixes of the convolution process. For example the values obtained after the last pooling P5 can be interpreted as probability values for classification objects KO and assign the deconvolution process to the reordering of the classified objects accordingly to the entered recorded image B.

In this example a result image EB is obtained as result data ED, in which the information of the initial recorded image BA is shown as classified objects.

Figure 4:
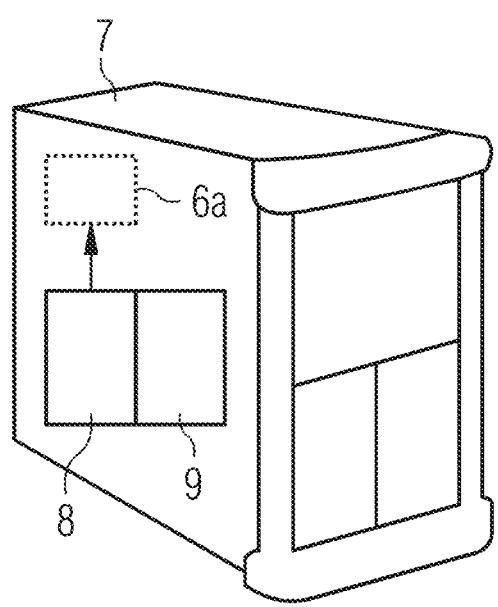
FIG. 4 shows a schematic diagram of an example embodiment of a preferred machine learning device.

FIG. 4 shows a schematic diagram of a preferred machine learning device 7. This machine learning device 7 comprises a processor 8 and a data memory 9, which are shown here as blocks. The data memory 9 contains instructions, which, when executed, make it possible for the processor 8 to detect a training image dataset TS provided to the processing device and to enter the training input images TE and training output images TA of the training image dataset TS into a convolutional neural network FN. Furthermore the machine learning device 7 is designed for operating a convolutional neural network FN and for training of an untrained convolutional neural network FN into a start compensation unit 6a, e.g. in accordance with a form of embodiment of the inventive method as shown in FIGS. 1 and 2.

Figure 5:
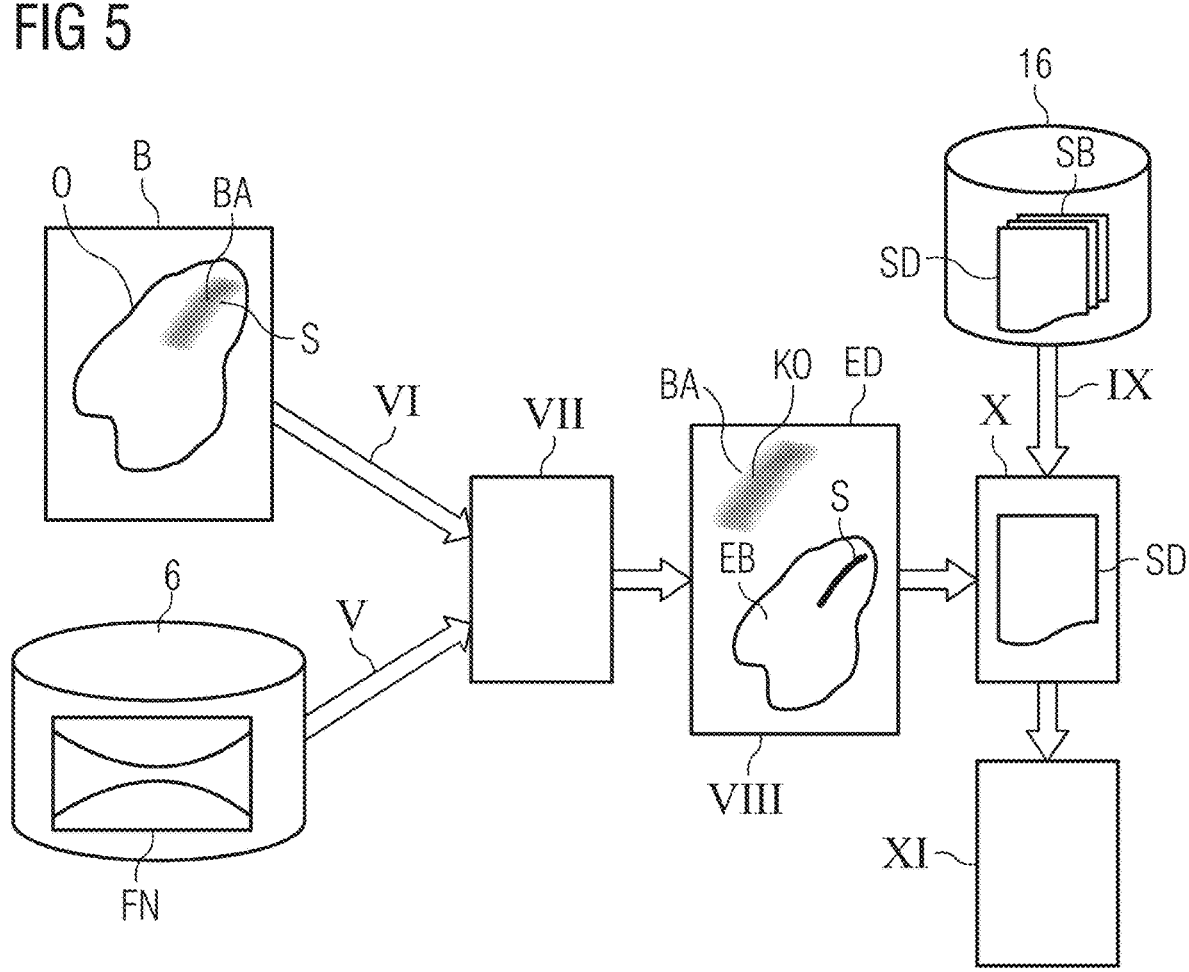
FIG. 5 shows a flow diagram for a possible execution sequence of an example embodiment of an inventive identification method.

FIG. 5 shows a flow diagram for a possible execution sequence of an inventive identification method for a current recorded medical image B to be checked or analyzed. This recorded image B can have been recorded for example via a medical imaging system 1, as is shown in FIG. 5.

In step V a compensation unit 6 is provided, which for example has been produced by a method as shown in FIG. 1 or 2.

In step VI a current recorded image B of an object O to be checked or analyzed is provided. This recorded image B is a recording made via a medical imaging system 1 for example. In this case a structure S is shown in the recorded image B, which has a motion artifact BA because of a movement of the object O.

In step VII the motion artifact BA is identified by way of the convolutional neural network FN of the compensation unit 6.

In step VIII there is an automatic annotation of the identified motion artifact BA. Result data ED is created, which comprises a result image here, in which the structure S concerned is shown without motion artifact BA, i.e. the motion artifact BA is compensated for. In addition the structure S or the motion artifact BA is stored as a classification object KO in the result data ED.

Up to this step an example of a method for pure identification of or compensation for motion artifacts BA would be shown. But with automatic identification of motion artifacts BA, in addition or as an alternative to automatic identification or compensation, there can also be an automatic control of a medical imaging system 1, as illustrated by the further method steps. This method can also be employed when the object to be recorded is known and its motion pattern has been recognized by the trained compensation unit.

In the following (optional) step IX a control data library SB is provided, in which control datasets SD for a medical imaging system 1 are held. These control datasets SD have a data link to the results of the compensation unit 6 so that, depending on a motion artifact BA or a notification about an object O to be recorded, a control dataset SD can be selected.

In step X a control dataset SD is selected in accordance with the object O to be recorded or with the motion artifact BA recognized.

In step XI this selected control dataset SD is used for control of the medical imaging system 1 for a new recording of the motif of the recorded image B being examined. This enables the new recorded image B to be recorded with new parameters, which are specifically chosen to record the region concerned of the object according to specific requirements, e.g. an adapted recording time, a mode, in which part recordings of the object are created, a use of a number of recording units for creation of simultaneous part images or an adaptation of the recording intervals to the motion phases of the object.

Figure 6:
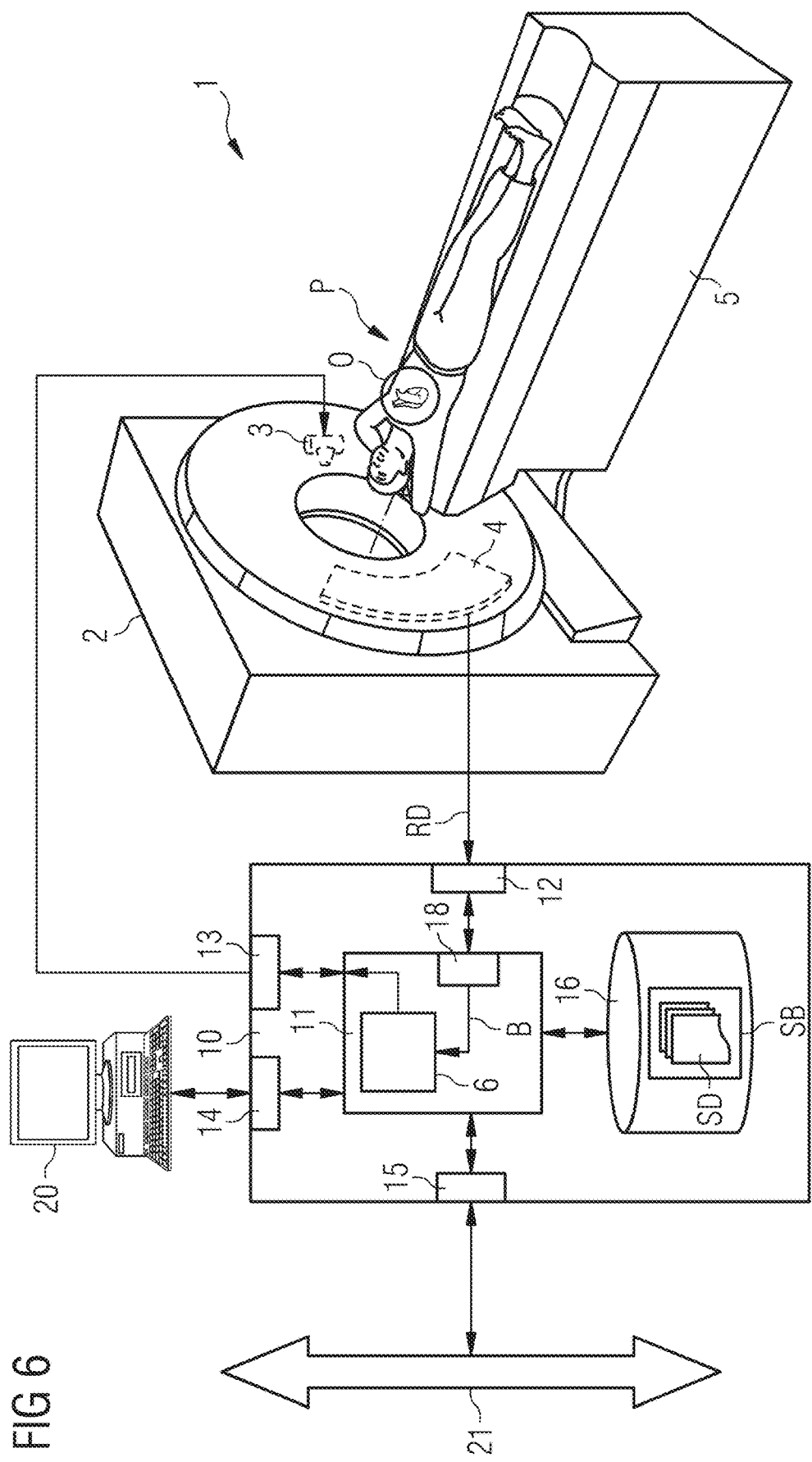
FIG. 6 shows a rough schematic diagram of a medical imaging system with an example embodiment of an inventive control device and compensation unit.

FIG. 6 shows a rough schematic of a medical imaging system 1 with an example embodiment of an inventive control device 10, which is designed to carry out a compensation for motion artifacts BA and preferably also to carry out a learning process according to an embodiment of an inventive method.

The computed tomography system 1 (CT), in the usual way, has a scanner 2 with a gantry in which an x-ray source 3 rotates, which irradiates a patient P in each case, who is pushed by way of a couch 5 into a measuring space of the gantry, so that the radiation strikes a detector 4 lying opposite the x-ray source 3 in each case. It is expressly pointed out that the example embodiment in accordance with FIG. 5 only involves an example of a CT and the invention can also be used on any other CTs.

Likewise, with the control device 10, the only components shown are those that are of significance for the explanation of the invention or are helpful for understanding it. Basically these types of CT systems and associated control devices are known to the person skilled in the art and therefore do not need to be explained in detail. In a dual-source CT system two x-ray sources 3 and two detectors 4 would be used.

It is pointed out that the invention can also be used on any other given medical imaging systems, e.g. with a magnetic resonance tomography system or with an ultrasound system, provided motion artifacts occur in said systems.

A core component of the control device 10 here is a processor 11, on which various components are realized in the form of software modules. The control device 10 furthermore has a terminal interface 14, to which a terminal 20 is connected, via which an operator can operate the control device 10 and thereby the computed tomography system 1. A further interface 15 is a network interface for connection to a data bus 21, in order in this way to establish a connection to an RIS or PACS (RIS: Radiology Information System; PACS: Picture Archiving and Communication System). For example image data from recorded images can be forwarded via this bus 21 or data (for example training image datasets TS) can be transferred.

The scanner 2 can be activated via a control interface 13 from the control device 10, i.e. the rotation speed of the gantry, the movement of the patient couch 5 and the x-ray source 3 itself can be controlled for example. The raw data RD is read out from the detector 4 via an acquisition interface 12.

Furthermore the control device 10 has a memory unit 16, in which a control data library SB with control datasets SD is held. The control datasets SD in this case can be linked to data such as that for motion artifacts BA or to data for an object to be recorded.

One component on the processor 11 is an image data reconstruction unit 18, with which the desired image data of the recorded images B of an object O will be reconstructed from the raw data RD obtained via the data acquisition interface 12. This image data reconstruction unit 18 forwards the reconstructed image data of a recorded image B to a compensation unit 6, in which first of all, in accordance with an inventive method, motion artifacts BA are identified or compensated for. As an alternative there is always the possibility of the compensation unit 6 working directly with the raw data RD and thus even being able to replace the image data reconstruction unit 18.

In the event of a motion artifact BA having occurred, which disproportionately falsifies the originally shown structure, or in the event that an object is to be recorded, of which the motion pattern is known to the compensation unit 6, a control dataset SD in accordance with at least one prespecified identification code is will be selected from the control data library (SB) provided by the memory unit 16 and using the selected control dataset SD a (possibly new) recorded image B of the object O created, in which preferably a compensation for motion artifacts BA is likewise undertaken. In this way a set of recorded images B can be created automatically, in which motion artifacts BA are correctly identified and if necessary have been compensated for in the optimum way.

In conclusion it is pointed out once again that the method described in detail above, as well as the devices shown, merely involve example embodiments, which can be modified by the person skilled in the art in a very wide diversity of ways, without departing from the area of the invention. Furthermore the use of the indefinite article "a" or "an" does not exclude the features involved also being able to be present more than once. Likewise the term "unit" and "module" does not exclude the components involved consisting of a number of interacting sub-components, which if necessary can also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for training a convolutional neural network of a compensation unit, the method comprising:
   provisioning a machine learning device, the machine learning device being designed for training the convolutional neural network;
   provisioning a start compensation unit, including an untrained convolutional neural network, on or at the machine learning device;
   provisioning a training image dataset including a plurality of medical training input images and at least one training output image, wherein a reference object is shown essentially without motion artifacts in the at least one training output image and the reference object concerned is contained in the plurality of medical training input images with different motion artifacts; and
   training the convolutional neural network of the compensation unit in accordance with a principle of machine learning, using the training image dataset.

2. The method of claim 1, wherein the at least one training output image of the training image dataset includes a plurality of training output images, each of the plurality of training output images including the reference object shown in a different phase of its motion.

3. The method of claim 1, wherein at least one of
   the reference object is annotated in the at least one training output image, and
   the at least one training output image includes information about at least one classification object of the reference object.

4. The method of claim 1, wherein the training image dataset is designed so that the plurality of medical training input images include part images of an overall image and, when combined, produce the overall image, and the at least one training output image contains the reference object shown on the overall image.

5. An identification method for automatic recognition of motion artifacts in a recorded medical image, comprising:
   provisioning a compensation unit with a neural network with a convolutional neural network trained by the method of claim 1;
   provisioning at least one recorded medical image;
   recognizing motion artifacts in the at least one recorded medical image via the compensation unit, by processing the at least one recorded medical image with the convolutional neural network; and
   creating result data with at least one of identification and reduction of the motion artifacts recognized.

6. The identification method of claim 5, wherein the result data comprises at least one of a result image and at least one classification object.

7. The identification method of claim 5, wherein a number of recorded medical images are provided, designed so that individual recorded images, of the number of recorded medical images, include part images of an overall image.

8. The identification method of claim 7, wherein the number of recorded medical images are computed tomography or x-ray images, and wherein individual recorded images, of the number of recorded medical images, have a reconstruction angle <180°, and a sum of the number of recorded medical images produces a reconstruction angle of 180°.

9. The identification method of claim 5, further comprising:
   provisioning a control data library, holding control datasets for a medical imaging system;
   selecting a control dataset based on a motion artifact recognized in the at least one recorded medical or on a choice of an object to be recorded; and
   using the control dataset selected to create a recorded image.

10. A control device for controlling a medical imaging system, comprising:
    at least one processor to designed to carry out the identification method of claim 5.

11. A medical imaging system, comprising:
    the control device of claim 10.

12. A non-transitory computer program product storing a computer program, directly loadable into a memory device of a processing system or of a control device of a medical imaging system, the computer program including program sections for carrying out the method of claim 1 when the computer program is executed in the processing system or the control device.

13. A non-transitory computer-readable medium, storing program sections readable in and executable by a processing unit, to carry out the method of claim 1 when the program sections are executed by the processing unit.

14. The method of claim 2, wherein at least one of
   the reference object is annotated in the plurality of training output images, and
   the plurality of training output images includes information about at least one classification object of the reference object.

15. The method of claim 4, wherein the training image dataset includes computed tomography or x-ray recordings.

16. The method of claim 15, wherein the computed tomography or x-ray recordings are of a dual-source CT or multi-source CT.

17. The method of claim 4, wherein individual ones of the plurality of medical training input images include a reconstruction angle <180°, a sum of a number of the plurality of medical training input images producing a reconstruction angle of 180°.

18. The identification method of claim 7, wherein the part images of the overall image produce the overall image, when combined.

19. A non-transitory computer program product storing a computer program, directly loadable into a memory device of a processing system or of a control device of a medical imaging system, the computer program including program sections for carrying out the method of claim 5 when the computer program is executed in the processing system or the control device.

20. A non-transitory computer-readable medium, storing program sections readable in and executable by a processing unit, to carry out the method of claim 5 when the program sections are executed by the processing unit.

21. A compensation unit for at least one of automatic identification of motion artifacts and compensation for motion artifacts in a recorded medical image, comprising:
   a convolutional neural network, trained by at least:
      provisioning a machine learning device, the machine learning device being designed for training the convolutional neural network;
      provisioning a start compensation unit, including an untrained convolutional neural network, on or at the machine learning device;
      provisioning a training image dataset including a plurality of medical training input images and at least one training output image, wherein a reference object is shown essentially without motion artifacts in the at least one training output image and the reference object concerned is contained in the plurality of medical training input images with different motion artifacts; and
      training the convolutional neural network of the compensation unit in accordance with a principle of machine learning, using the training image dataset.

22. A machine learning device, comprising:
a processor; and
a data memory, storing instructions which, when executed, configured the processor to at least:
   enter a training image dataset provided to the processor into a convolutional neural network;
   operate the convolutional neural network; and
   train a start compensation unit with an untrained convolutional neural network according to a method for training convolutional neural network of a compensation unit, the method comprising:
      provisioning a machine learning device, the machine learning device being designed for training the convolutional neural network;
      provisioning a start compensation unit, including an untrained convolutional neural network, on or at the machine learning device;
      provisioning a training image dataset including a plurality of medical training input images and at least one training output image, wherein a reference object is shown essentially without motion artifacts in the at least one training output image and the reference object concerned is contained in the plurality of medical training input images with different motion artifacts; and
      training the convolutional neural network of the compensation unit in accordance with a principle of machine learning, using the training image dataset.

* * * * *